(12) United States Patent
Arai et al.

(10) Patent No.: US 6,887,196 B2
(45) Date of Patent: May 3, 2005

(54) ENDOSCOPE APPARATUS WITH AN OMNIDIRECTIONAL VIEW FIELD AND A TRANSLATABLE ILLUMINATOR

(75) Inventors: Minoru Arai, Saitama (JP); Kunihiko Miyagi, Wako (JP)

(73) Assignee: Machida Endoscope Co., Ltd. (JP)

( * ) Notice: Subject to any disclaimer, the term of this patent is extended or adjusted under 35 U.S.C. 154(b) by 58 days.

(21) Appl. No.: 10/393,231

(22) Filed: Mar. 20, 2003

(65) Prior Publication Data

US 2003/0191369 A1 Oct. 9, 2003

(30) Foreign Application Priority Data

Mar. 25, 2002 (JP) ........................ 2002-082772

(51) Int. Cl.[7] .................................................. A61B 1/06
(52) U.S. Cl. ........................ 600/178; 600/170; 600/177; 600/182
(58) Field of Search ................................ 600/129–130, 600/160, 166, 170–171, 173, 175–177, 182; 348/84–85; 356/241; 359/367

(56) References Cited

U.S. PATENT DOCUMENTS

| | | | | |
|---|---|---|---|---|
| 5,961,445 A | * | 10/1999 | Chikama | 600/112 |
| 6,074,342 A | | 6/2000 | Odanaka et al. | |
| 6,174,307 B1 | * | 1/2001 | Daniel et al. | 606/15 |
| 6,293,910 B1 | * | 9/2001 | Yamakita et al. | 600/132 |
| 6,387,044 B1 | * | 5/2002 | Tachibana et al. | 600/114 |
| 6,408,889 B1 | | 6/2002 | Komachi | |
| 6,461,330 B1 | | 10/2002 | Miyagi | |
| 6,503,196 B1 | * | 1/2003 | Kehr et al. | 600/176 |

FOREIGN PATENT DOCUMENTS

| | | |
|---|---|---|
| DE | 199 42 080 A1 | 3/2001 |
| EP | 0 745 347 A2 | 4/1996 |
| JP | 10-318727 | 12/1998 |
| JP | 3086204 | 9/2000 |
| WO | WO 99/16341 A | 4/1999 |

* cited by examiner

*Primary Examiner*—John Leubecker
*Assistant Examiner*—Philip R Smith
(74) *Attorney, Agent, or Firm*—Brown & Michaels, PC; Eugene Stephens & Associates

(57) ABSTRACT

An omnidirectional endoscope device 1 is provided at a distal end part of an insertion section 12 of an endoscope 10 with an omnidirectional light receiving unit 20 for receiving an incident light from all around the periphery in the peripheral direction and reflecting the light toward a relay lens optical system 13. The insertion section 12 slidably pierces through a retaining cylinder 33. A light guide 35 (illumination light transmitting means) is embedded in the retaining cylinder 33, and an outgoing surface at the distal end of this light guide 35 is faced with a distal end face of the retaining cylinder 33. The retaining cylinder 33 can be operated in a sliding manner by a grip 31 disposed at the basal end. By this, the illumination light can strike upon the view field of the omnidirectional light receiving mechanism regardless whether the inside space of an image to be observed is large or small.

6 Claims, 4 Drawing Sheets

ENDOSCOPE APPARATUS WITH AN OMNIDIRECTIONAL VIEW FIELD AND A TRANSLATABLE ILLUMINATOR

BACKGROUND OF THE INVENTION

The present invention relates to an omnidirectional endoscope apparatus having a viewfield covering all around the periphery in the peripheral direction.

An endoscope is effective as an apparatus for observing the inner periphery of a narrow and/or elongated space such as the inside of a cylinder block of an engine and the inside of piping, for example. On the other hand, since a typical endoscope has a limited view field angle, such operation as to turn the endoscope is required for the user in order to observe all around the periphery. In this respect, an omnidirectional endoscope which can receive an incident light from all around the periphery in the peripheral direction and take it into image transmitting means is effective because the user can see all around the periphery at a time. As one example of such an omnidirectional endoscope, an endoscope is known which is equipped with, for example, a conical prism placed at a distal end of its insertion section. A distal end face of a light guide (illumination light transmitting means) occupies a position slightly on the basal end side of the conical prism. An illumination light is radially emitted obliquely forward from this distal end face and illuminates an object to be observed. (See the Japanese Patent Application Unexamined (Laid-Open) Publication No. H10-318727.)

In the above known omnidirectional endoscope, the light guide is fixedly embedded in the insertion section. Accordingly, the positional relation between the distal end face of the light guide and the conical prism is held constant. For this reason, it has such a problem that an image looks dark because when the inside diameter of a space of the object to be observed is small, the illumination light strikes upon the inner peripheral surface of the space more on the basal end side than the view field region, and when the inside diameter of the space is large, the illumination light strikes upon the inner peripheral surface of the space more on the distal end side than the view field region.

SUMMARY OF THE INVENTION

In order to solve the above problem, the present invention provides an omnidirectional endoscope having a view field covering all around the periphery in the peripheral direction, comprising a main body section, an insertion section extending from the main body section, an omnidirectional light receiving mechanism disposed at a distal end part of the insertion section and for receiving an incident light coming from all around the periphery in the peripheral direction and reflecting it towards a basal end, image transmitting means received in the main body section and the insertion section and for transmitting light coming from the omnidirectional light receiving mechanism, and an illumination light transmitting mechanism. The illumination light transmitting mechanism includes illumination light transmitting means, a retaining part and a slide control part. The illumination light transmitting means extends along the insertion section. This illumination light transmitting means transmits an illumination light and output it from the distal end face of the illumination light transmitting means. The retaining part is slidably fitted to the outer periphery of the insertion section. The retaining part retains the illumination light transmitting means, at least a distal end of which is in the form of a ring.

The slide control part is disposed at the basal end of the insertion section or at the main body section. Moreover, the slide control part is connected to the retaining part. By this slide control part, the retaining part can be slid along the insertion section and thus, the distal end part of the illumination light transmitting means can be slid along the insertion section.

Owing to the above arrangement, it can be operated such that when the inside space of an object to be observed is small, the retaining part is slid towards the distal end in order to bring the outgoing position of the illumination light toward the omnidirectional light receiving mechanism and when the inside space of the object is large, the retaining part is slid toward the basal end in order to bring the outgoing position of the illumination light away from the omnidirectional light receiving mechanism. By doing so, the illumination light can strike upon the view field of the omnidirectional light receiving mechanism. Thus, a clear and bright image can be obtained.

Preferably, the retaining part is in the form of a cylinder for allowing almost the entire insertion section to slidably pierce therethrough, the illumination light transmitting means is embedded in the retaining part over its entire length, a ring-like distal end face of the illumination light transmitting means is faced with the distal end face of the retaining part, the slide control part is in the form of a cylinder for allowing the basal end part of the insertion section or the main body section to slidably pierce therethrough and connected to the basal end part of the retaining part, and the illumination light transmitting mechanism is separatable from the main body section and the insertion section.

Owing to the above arrangement, the illumination light transmitting mechanism can be simplified in structure and can be replaced easily.

Preferably, the omnidirectional light receiving mechanism includes a transparent cylindrical observing window, a convex mirror received in the observing window and for reflecting an incident light coming from the observing window toward the basal end and thus toward the image transmitting means, and a rod-like body disposed at a top part of the convex mirror in such a manner as to project toward the basal end, the rod-like body being adapted to absorb the light passing across the inside space of the observing window which light would otherwise be reflected on the inner peripheral surface of the observing window and proceed toward the convex mirror.

Owing to the above arrangement, clearness of the image can be enhanced. That is, clearness of the image can be prevented from being degraded, and an image on the opposite side can be prevented from being reflected.

Preferably, the observing window is provided at an outer periphery on the basal end side with a ring-like light shielding member such that the ring-like light shielding member projects radially, and this light shielding member shields the illumination light which would otherwise be made incident into the observing window from the distal end face of the illumination light transmitting means.

Owing to the above arrangement, contract of the image can surely be prevented from lowering.

Preferably, the observing window extends toward the distal end beyond the convex mirror, and a ring-like light absorbing member is disposed at an outer periphery of the extending part of the observing window.

Owing to the above arrangement, a halation can be prevented from occurring at the peripheral edge part of the convex mirror.

Preferably, the omnidirectional light receiving mechanism is removably attached to the insertion section.

Owing to the above arrangement, the omnidirectional light receiving mechanism can easily be replaced with a new one or another omnidirectional light receiving mechanism having different specifications.

DETAILED DESCRIPTION OF THE EMBODIMENTS

One embodiment of the present invention will be described hereinafter with reference to the accompanying drawings.

Figure 1:
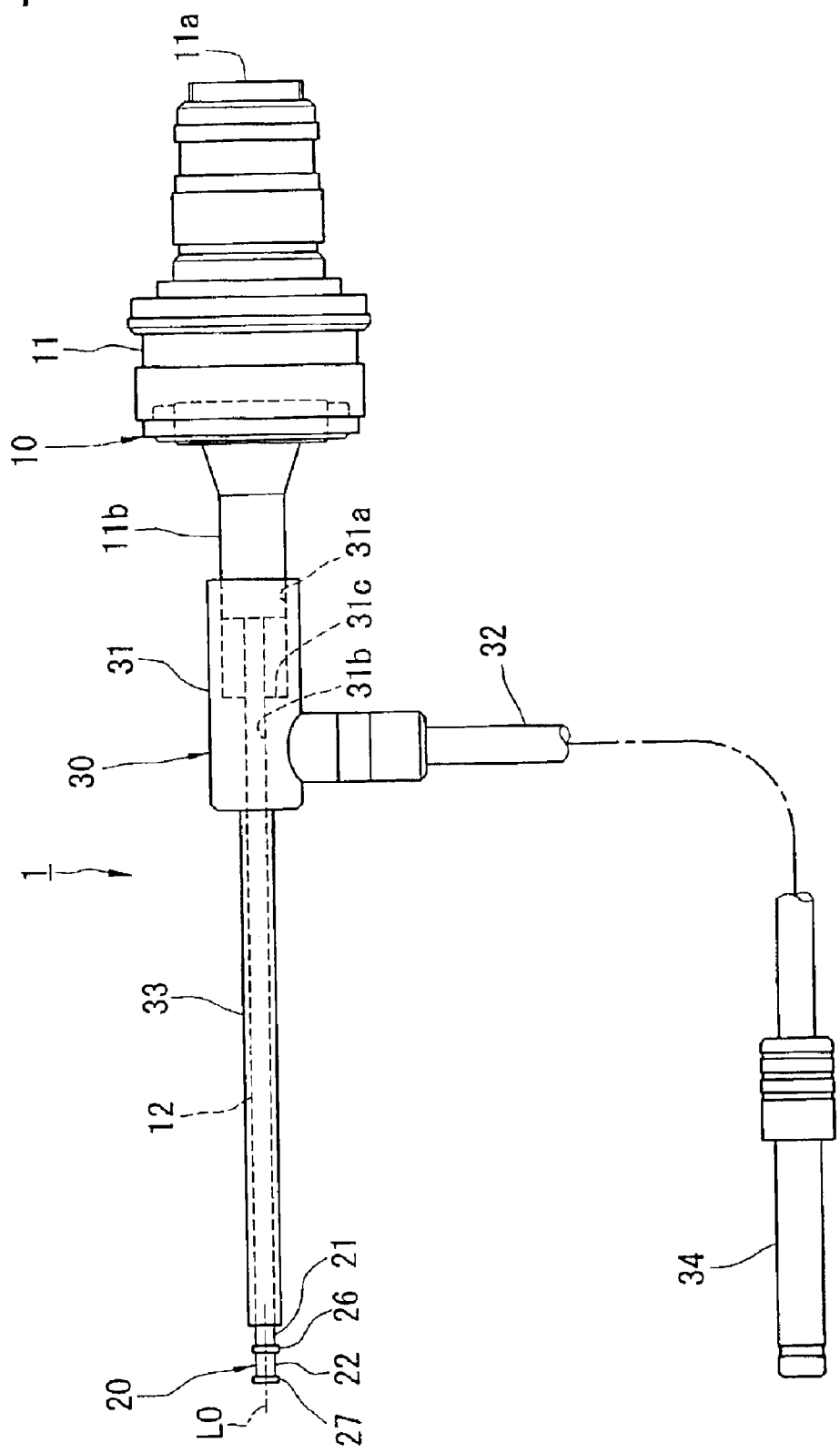
FIG. 1 is a side view of an omnidirectional endoscope apparatus according to one embodiment of the present invention.
Figure 2:
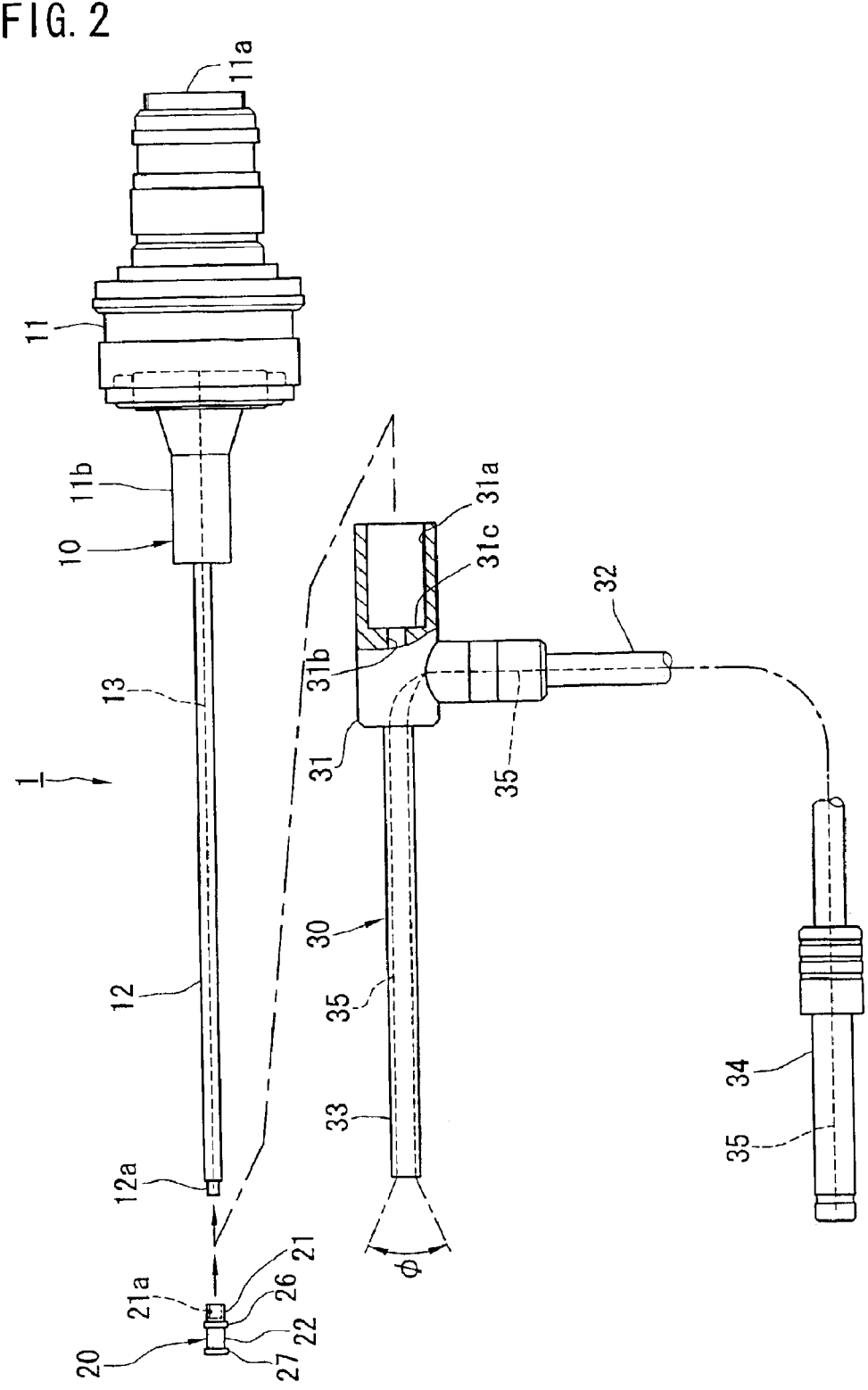
FIG. 2 is a side view showing the above omnidirectional endoscope apparatus in its exploded manner.

FIGS. 1 and 2 show an omnidirectional endoscope apparatus 1. The omnidirectional endoscope apparatus 1 comprises an endoscope 10, an omnidirectional light receiving unit 20 (omnidirectional light receiving mechanism), and an illumination light transmitting unit 30 (illumination light transmitting mechanism). Those component elements 10, 20, 30 are removably united together.

The endoscope 10 includes a main body section 11 having an eyepiece part 11a, and a metal-made insertion section 12 extending linearly along an axis LO from a tip shaft 11b of the main body section 11. The material of the insertion section 12 is not limited to hard metal but it may be flexible material such as resin.

A relay lens optical system 13 (image transmission means) is received in the main body section 11 and insertion section 12. The basal end of the relay lens optical system 13 is optically connected to the eyepiece 11a. The tip part of the relay optical system 13 is optically connected to an objective optical system (not shown) and thus to the omnidirectional light receiving unit 20 which objective optical system is received in the tip part of the insertion section 12. Instead of the relay lens optical system 13, an image guide composed of a bundle of plural optical fibers may be used as the image transmission means.

Figure 3:
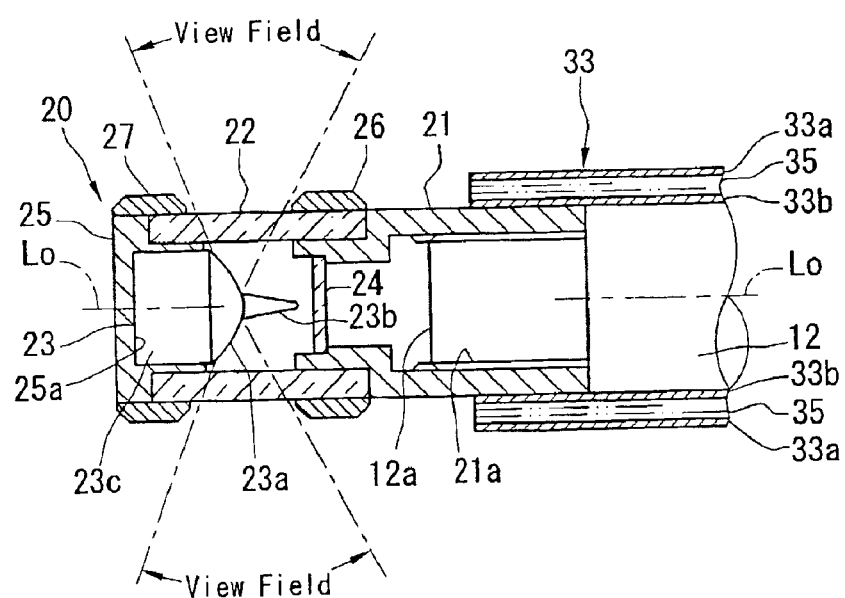
FIG. 3 is a sectional view of a tip part of the omnidirectional endoscope apparatus.

As shown in FIG. 3, the omnidirectional light receiving unit 20 includes a metal-made connecting cylinder 21, a circular cylindrical observing window 22 which is made of transparent glass, resin or the like and connected to the tip part of the connecting cylinder 21, and a light receiving member 23. A female thread 21a is formed at the inner peripheral surface of the connecting cylinder 21. This female thread 21a is threadingly engaged with a male thread 12a formed at the tip of the insertion section 12 of the endoscope 10. Owing to this arrangement, the connecting cylinder 21 and thus the circular cylindrical observing window 22 is connected to the insertion section 12 on a co-axis LO. A cover glass 24 is fitted to a tip opening facing the inside of the observing window 22 in the connecting cylinder 21.

Light enters the circular cylindrical observing window 22 through all around the periphery in the peripheral direction.

The circular cylindrical observing window 22 is subjected to the purpose for retaining the light receiving optical member 23. The light receiving optical member 23 is received in the circular cylindrical observing window 22. The tip opening of the circular cylindrical observing window 22 is blocked with a cap 25. The light receiving member 23 is fixed to this cap 25.

The light receiving member 23 is made of metal, glass, resin or the like. The light receiving member 23 integrally includes a basal part 23c, a convex mirror 23a, and a rod-like body 23b. The basal part 23c has a circular columnar configuration coaxial with the window 22 and thus the insertion section 12 and fitted to a fitting recess 25a of the cap 25. The convex mirror 23a is formed on a basal end face of the basal part 23b. The convex mirror 23a has a viewfield spreading sideways in the form of a sector on a plane along the axis LO. This viewfield is spread so wide as 360 degrees around the axis LO.

The convex mirror 23a is provided at its apex with the above-mentioned rod-like body 23b which projects toward the basal end. The rod-like body 23b has an elongated conical configuration (rod-like or needle-like configuration) along the axis LO of the window 22 and thus, along the insertion section 12. Matt/black color treatment for absorbing light is applied to the surface of the rod-like body 23b.

The cylindrical observing window 22 is extended towards the tip beyond the boundary between the convex mirror 23a and basal part 23c of the light receiving member 23. A light absorbing ring 27 (light absorbing member) is fitted to the outer peripheral surface of the extension part of the observing window 22 in such a manner as not to intervene the viewfield of the convex mirror 23a. The light absorbing ring 27 is also fitted to the outer peripheral surface of the cap 25. A black color film for absorbing light is applied to the entire surface (outer peripheral surface, chamfering part, end faces and inner peripheral surface) of the light absorbing ring 27.

On the other hand, a light shielding ring 26 (light shielding member) is fitted to the outer periphery on the basal end side of the observing window 22 in such a manner as not to intervene the viewfield of the convex lens 23a. A black color film for absorbing light is applied to the entire surface (outer peripheral surface, chamfering part, end faces and inner peripheral surface) of the light shielding ring 26.

The illumination light transmitting unit 20 will be described, next.

As shown in FIG. 2, the illumination light transmitting unit 30 includes a cylindrical grip (slide control part) 31, a flexible light guide cable 32 extending from one side of this grip 31, and a retaining cylinder 33 (retaining part) linearly extending from the tip part of the grip 31.

A step 31c having an enlarged-diameter bore 31a on its basal end side and a reduced-diameter bore 31b on its distal end side, is formed on the inner peripheral surface of the grip 31.

The cable 32 is provided at its distal end with a light guide plug 34. This plug 34 is connected to a light source (not shown) of illumination light.

As shown in FIG. 3, the retaining cylinder 33 has a dual structure composed of an outer tube 33a and an inner tube 33b which are made of thin metal. The material of tubes 33a, 33b is not limited to hard metal. Instead, the tubes 33a, 33b may be made of flexible material such as resin.

As shown in FIG. 2, a light guide 35 (illumination light transmission means) composed of a bundle of plural optical fibers is received in the plug 34, the cable 32, the distal end side of the grip 31 and the retaining cylinder 33. The light guide 35 is in the shape of a circle in section at the insides of the plug 34 and cable 32 and is spread in the form of a hollow circle in section at the distal end side of the grip 31 toward the retaining cylinder 33. As shown in FIG. 3, the light guide 35 is embedded in the retaining cylinder 33 in such a manner as to be sandwiched between the outer tube 33a and the inner tube 33b.

The distal end face of the light guide 35 is exposed to the distal end face of the retaining cylinder 33. Owing to this arrangement, the illumination light coming from the light source is, as shown in FIG. 2 traveled along the light guide 35 and radially outputted obliquely forward (toward the distal end) from the distal end face of the light guide 35, at an outgoing angle $\phi$ which is established in accordance with the numerical aperture NA of the light guide 35. A protective cover glass may be mounted on the distal end face of the light guide 35.

As shown in FIG. 1, when the omnidirectional endoscope device 1 is in a condition for use, the grip 31 and retaining cylinder 33 of the illumination light transmitting unit 30 allow the main body section 11 and insertion section 12 of the endoscope 10 to slidably pierce therethrough along the axis LO. That is, the tip shaft 11b of the main body section 11 pierces through an enlarged-diameter hole 31a on the basal end side of the grip 31, and the insertion section 12 pierces through a reduced-diameter hole 31a on the distal end side of the grip 31 and the retaining cylinder 33. The grip 31 and the retaining cylinder 33 of the illumination light transmitting unit 30 can slide toward the basal end until a step 31c of the grip 31 is abutted with a distal end of the shaft 11b and a basal end face of the grip 31 is abutted with a tapered part of the shaft 11b. Also the grip 31 and the retaining cylinder 33 can slide toward the distal end until the distal end of the retaining cylinder 33 is abutted with the light shielding ring 26 of the omnidirectional light receiving unit 20. (The grip 31 and the retaining cylinder 33 can also rotate about the axis LO of the endoscope 10.) When the omnidirectional light receiving unit 20 is removed from the endoscope 10, the illumination light transmitting unit 30 can further be slid toward the distal end so as to be removed from the endoscope 10. At the time of assembling the omnidirectional endoscope device 1, the endoscope 10 is inserted into the illumination light transmitting unit 30 first and thereafter, the omnidirectional light receiving unit 20 is attached to the endoscope 10.

A method for observing, for example, the inner peripheral surface of a tube by the omnidirectional endoscope device 1 thus constructed will now be described. Of course, the device 1 is preliminarily assembled prior to observation.

Figure 4:
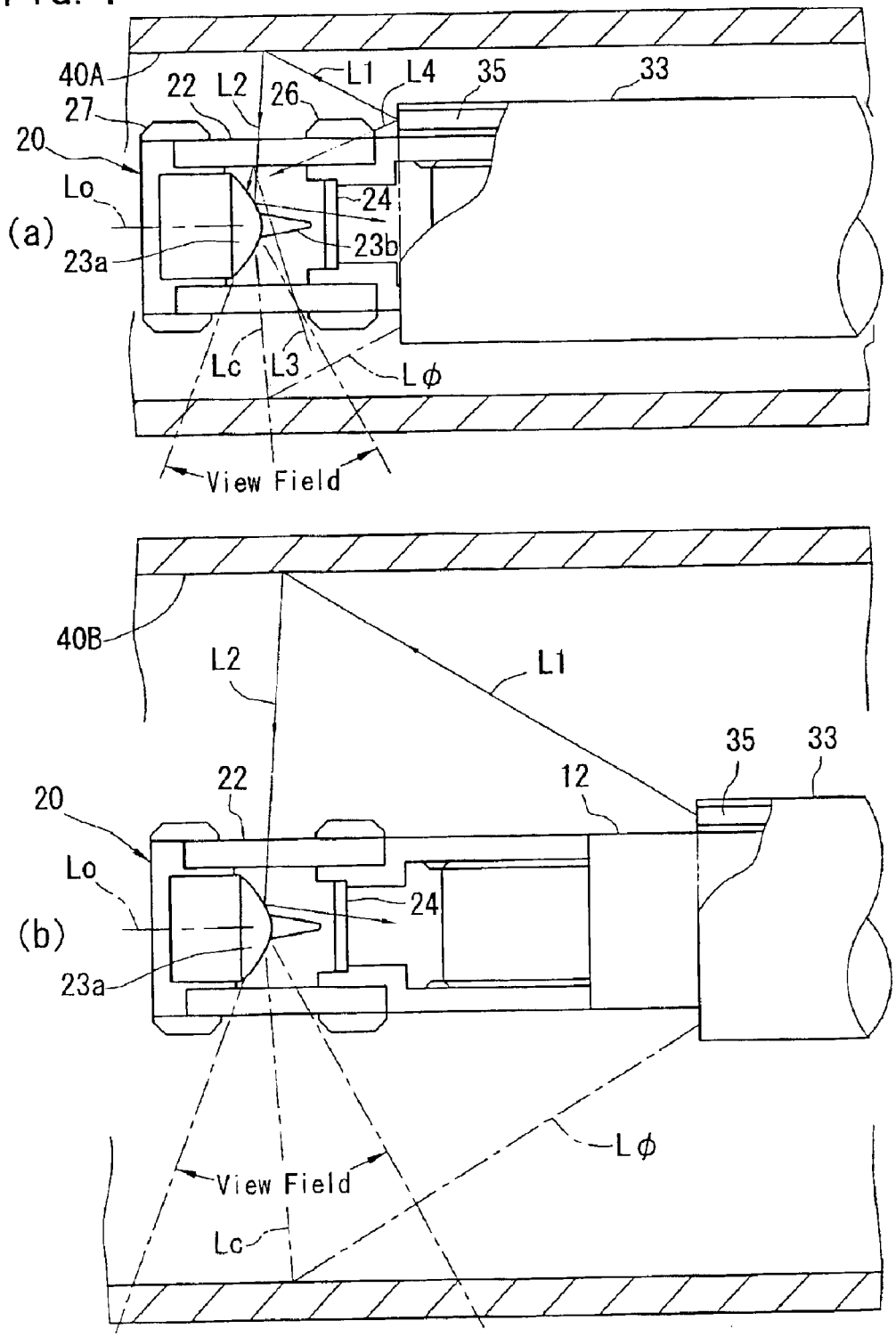
FIG. 4(a) is a sectional view, like FIG. 3, showing the ways of observing the inner peripheral surface of a reduced-diameter tube through the omnidirectional endoscope apparatus.
FIG. 4(b) is a sectional view, like FIG. 3, showing the ways of observing the inner peripheral surface of an enlarged-diameter tube through the omnidirectional endoscope apparatus.

FIG. 4(a) shows the ways of observing a reduced-diameter tube 40A having a comparatively small diameter. The device 1 is inserted into the reduced-diameter tube 40A first with the omnidirectional light receiving unit 20 and then the insertion section 12 and retaining cylinder 33. Since the object is small in diameter, the grip 31 at hand is then slid toward the distal end (toward the inside of the reduced-diameter tube 40A) with respect to the endoscope main body section 11 and thus, the retaining cylinder 33 is brought toward the omnidirectional light receiving unit 20. At that time, it is desirous that the light guide 35 and the distal end face of the retaining cylinder 33 are located such that a center line direction Lc of the view field of the convex mirror 23a in a plane along the axis LO is intersected with an outgoing angle direction L $\phi$ of the light guide 35 almost at the inner peripheral surface of the reduced-diameter tube 40A. Owing to this arrangement, an illumination light L1 coming from the distal end face of the light guide 35 can strike upon the entire area of that part of the inner peripheral surface of the tube 40 which entire area corresponds to the view field of the convex mirror 23a, and therefore, the illumination light L1 can illuminate the entire view field.

An image light L2 from the inner peripheral surface of the reduced-diameter tube 40A is made incident into the inner space of the cylindrical observing window 22 and reflected by the convex mirror 23a toward the basal end. Then, the light L2 passes through a cover glass 24 and an objective optical system at the distal end of the insertion section 12 in order and then, the light L2 is taken into the relay lens optical system 13. Thereafter, the light L2 is transmitted to an eyepiece part 11a. Hence, by peeping through the eyepiece part 11a, the illuminated inner peripheral surface of the reduced-diameter tube 40A can be observed.

The image light L2 is made incident into the cylindrical observing window 22 from the directions of 360 degrees around the side periphery and this image light L2 coming from the directions of 360 degrees is reflected toward the insertion section 12 by the convex mirror 23a. Accordingly, an image all around the periphery of the inner peripheral surface can be observed at a time. By this, observing efficiency can be enhanced.

FIG. 4(b) shows the ways of observing an enlarged-diameter tube 40B having a comparatively large diameter. In this case, the grip 21 is slid toward the basal end with respect to the endoscope main body section 11 and thus, the retaining cylinder 33 is brought away from the omnidirectional light receiving unit 20. By this, as in the same with the reduced-diameter tube 40A, it can be arranged such that a center line direction Lc of the view field of the convex mirror 23a is intersected with an outgoing angle direction L $\phi$ of the light guide 35 almost at the inner peripheral surface of the enlarged-diameter tube 40B. Owing to this arrangement, the entire area of that part of the inner peripheral surface of the tube 40B which entire area corresponds to the view field of the convex mirror 23a can be illuminated by the illumination light L1, and thus, an image over the entire area of the view field can be observed through the eyepiece part 11a.

As a result, a clear and bright image can be obtained regardless whether the inside spaces of the objects 40A, 40B to be observed are large or small, and convenience and versatility of the omnidirectional endoscope device can be enhanced extensively.

Since the illumination light L1 obliquely strikes the inner peripheral surfaces of the tubes 40A, 40B, irregularities, such as cuts or scratches formed, if any, on the inner peripheral surface appear in the form of a shade and so, they can easily be discovered. When the grip 31 of the illumination light transmitting unit 30 is slightly moved back and forth with the endoscope 10 positionally fixed with respect to the tubes 40A, 40B, inclination of the illumination light L1 varies and the above-mentioned shade moves. Therefore, irregularities such as cuts or scratches can more easily be discovered, and inspection efficiency can be enhanced.

As shown in FIG. 4(a), the image light L2 straightly strikes upon the convex mirror 23a from the objects 40A, 40B. Of all the light, which is made incident into the observing window 22, there is light, like light L3, which passes across the inside space of the observing window 22. The light L3, if not absorbed during the time it passes across the inside space of the observing window 22, would be reflected on the inner peripheral surface opposing to the incoming side and proceed toward the convex mirror 23a. When this light L3 should strike upon the convex mirror 23a, clarity of the image of the object to be observed would be degraded and an image on the opposite side would be formed. However, the light L3 strikes upon the rod-like body 23b during the time it passes across the inside space of the observing window 22. By this, the light L2 can be absorbed before it strikes upon the inner peripheral surface of the window 22 and thus, the convex mirror 23a. This serves to prevent the clarity of the image from being degraded and prevent the image on the opposite side from being formed.

The light absorbing performance made by the rod-like body 23b with respect to the light L3 which would otherwise be reflected on the inner surface of the cylinder is same as that disclosed in the Japanese Patent No. 3086204.

Among the illumination light coming from the light guide 35, there is a light L4 which is radiated inward and likely made incident directly into the observing window 22. However, such direct incoming illumination light L4 is blocked by the light shielding ring 26 provided on the basal end side of the observing window 22. Thus, the illumination light L4 is prohibited from being made incident directly into the observing window 22 and thus, into the convex mirror 23a. As a result, the contract of the images of the objects 40A, 40B can be prevented from being lowered. Moreover, since the light shielding ring 26 projects radially from the outer peripheral surface of the window 22, it can also prevent the illumination light, which is generally parallel to the axis LO but slightly inclined inward, from being made incident directly into the observing window 22. Furthermore, even if refraction directing inward occurs at the outer peripheral surface of the light shielding ring 26, such light can be prevented from being made incident into the observing window 22. By this, the contrast of the image can surely be prevented from being lowered.

Moreover, by the light absorbing ring 27 disposed at the outer periphery of the extending part of the distal end of the observing window 22, a halation can be prevented from occurring at the boundary, or its nearby area, between the convex mirror 23a and the basal part 23c. Many reasons can be considered why the light absorbing ring 27 can act to prevent the occurrence of a halation. Anyway, through experiments carried out by the present inventors, significant effects were obtained. Specifically, in case no extending part was provided at the observing window 22 and the distal end face was located at the boundary, or its nearby area, between the convex mirror 23a and the basal part 23c, a comparatively large halation occurred. In case an extending part was provided at the observing window 22 and the distal end face was located at a position offset towards the distal end side from the boundary but the light absorbing ring 27 was not employed, the halation was small but it could not be totally eliminated. In case the light absorbing ring 27 was additionally provided at the extending part of the observing window 22, the halation could substantially be eliminated as mentioned previously.

Two rings 26, 27 undertake the role for protecting the observing window 22 in addition to the above-mentioned various functions.

Since the omnidirectional light receiving unit 20 is removably attached to the insertion section 12, it can easily be replaced with a new omnidirectional light receiving unit 20 or an omnidirectional light receiving mechanism having different specifications.

The present invention is not limited to the above embodiments, but many changes and modifications can be made in accordance with necessity.

For example, the illumination light transmitting means of the illumination transmitting mechanism is good enough only if at least the distal end part is in the form of a ring capable of surrounding the insertion section of the endoscope. The retaining part is good enough only if it retains the illumination transmitting means at least a distal end part of which is in the form of a ring. It is accepted that the retaining part disposed at the distal end part of the insertion section and the slide control part disposed at the insertion section or main body section are connected to each other through a connecting member disposed at the insertion section. It is also accepted that the retaining part is caused to slide along the insertion section by a mechanical or electrical slide mechanism, and the slide control part controls the slide mechanism. The distal ends of the retaining part and illumination light transmitting means may be slanted.

In case the retaining part is in the form of a cylinder extending generally over the entire length of the insertion section, the basal end part of the retaining part may also serve as the slide control part.

The halation preventing light absorbing member disposed at the extending part of the distal end of the cylindrical observing window is not limited to a thick member such as the light absorbing ring 27 but it may be a thin light absorbing film-like member.

The mechanism for attaching/removing the insertion section and the omnidirectional light receiving mechanism is not limited to the screws 12a, 21a but it may take a wide variety of forms.

What is claimed is:

1. An omnidirectional endoscope device having a view field covering all around the periphery in the peripheral direction, comprising a main body section; an insertion section extending from said main body section; an omnidirectional light receiving mechanism disposed at a distal end part of said insertion section and for receiving an incident light coming from the entire periphery at the same time in the peripheral direction and reflecting it towards a basal end; image transmitting means for transmitting light coming from said omnidirectional light receiving mechanism; and an illumination light transmitting mechanism;

said illumination light transmitting mechanism including illumination light transmitting means extending along said insertion section and for transmitting the illumination light so as to be outputted from a distal end face of said illumination light transmitting means; a retaining part for retaining said illumination light transmitting means, at least a distal end part of which is in the form of a ring, and slidably fitted to an outer periphery of said insertion section; and a slide control part connected to said retaining part and disposed at a basal part of said insertion section or at said main body section and for sliding said retaining part and thus a distal end part of said illumination light transmitting means along said insertion section.

2. An omnidirectional endoscope device according to claim 1, wherein said retaining part is in the form of a cylinder for allowing almost the entire insertion section to slidably pierce therethrough, said illumination light transmitting means is embedded in said retaining part over its entire length, a ring-like distal end face of the illumination light transmitting means is faced with the distal end face of said retaining part, said slide control part is in the form of a cylinder for allowing the basal end part of said insertion section or said main body section to slidably pierce therethrough and connected to the basal end part of said retaining part, and said illumination light transmitting mechanism is separatable from said main body section and said insertion section.

3. An omnidirectional endoscope device according to claim 1, wherein said omnidirectional light receiving mechanism includes a transparent cylindrical observing window, a convex mirror received in said observing window and for reflecting an incident light coming from said observing window toward the basal end and thus toward said image transmitting means, and a rod-like body disposed at a top part of said convex mirror in such a manner as to project toward the basal end, said rod-like body being adapted to absorb the light passing across the inside space of said observing window which light would otherwise be reflected on the inner peripheral surface of said observing window and proceed toward said convex mirror.

4. An omnidirectional endoscope device according to claim 3, wherein said observing window is provided at an outer periphery on the basal end side with a ring-like light shielding member such that said ring-like light shielding member projects radially, and said light shielding member shields the illumination light which would otherwise be made incident into said observing window from the distal end face of said illumination light transmitting means.

5. An omnidirectional endoscope device according to claim 3, wherein said observing window extends toward the distal end beyond said convex mirror, and a ring-like light absorbing member is disposed at an outer periphery of the extending part of said observing window.

6. An omnidirectional endoscope device according to claim 1, wherein said omnidirectional light receiving mechanism is removably attached to said insertion section.

* * * * *